United States Patent [19]
Wright

[11] Patent Number: 4,661,348
[45] Date of Patent: Apr. 28, 1987

[54] BABESIOSIS ANTIGEN AND METHOD FOR PREPARATION

[75] Inventor: Ian G. Wright, Sherwood, Australia

[73] Assignee: Commonwealth Scientific & Industrial Research Organization, Canberra, Australia

[21] Appl. No.: 631,547

[22] PCT Filed: Nov. 8, 1983

[86] PCT No.: PCT/AU83/00162

§ 371 Date: Jul. 24, 1984

§ 102(e) Date: Jul. 24, 1984

[87] PCT Pub. No.: WO84/01897

PCT Pub. Date: May 24, 1984

[30] Foreign Application Priority Data

Nov. 10, 1982 [AU] Australia ............................. PF6738

[51] Int. Cl.⁴ ........................................... A61K 39/018
[52] U.S. Cl. ....................................... 424/88; 435/68; 435/172.2
[58] Field of Search ...................... 424/88; 260/112 R; 435/68, 172.2

[56] References Cited

U.S. PATENT DOCUMENTS 4,457,915 7/1984 Goodger et al. ..................... 424/88
4,596,707 6/1986 Ristic et al. ........................... 424/88

FOREIGN PATENT DOCUMENTS 2062463 1/1981 United Kingdom .

OTHER PUBLICATIONS

Goff et al: "The Bovine Immune Response to Tick-Derived . . . ", *Veterinary Parasitology*, 11 (1982), pp. 109–120.
Todorovic et al: "Comparison of the Dried Blood on Filter Paper and Serum . . . ", Diagnosis of Bovine Babesiosis, Tropenmed. Parasit., 29 (1978), pp. 88–94.
De Vos: "Immunogenicity and Pathogenicity of Three South African Strains . . . ", Onderstepoort J. Vet. Res., 45 (2), pp. 119–124 (1978).
Kuttler et al: "Immunologenicity . . . in Freund's Complete Adjuvant", Am. J. Vet. Res., vol. 41, No. 4, pp. 536–537.
Haggard et al: "Immunologic Effects of Experimental Iodine . . . ", Am. J. Vet. Res., vol. 41, No. 4, pp. 537–538.
Perez et al: "Cell-Mediated Immune Response in Hamsters Infected with Babesia Microti", Veterinary Parasitology, 3 (1977), pp. 161–167.
Molinar et al: "Antigenic and Immunogenic Studies on Cell Culture . . . ", Veterinary Parasitology, 10 (1982), pp. 29–40.
Latif et al: "Effect of Age on the Immune Response of Cattle . . . ", Veterinary Parasitology, 5 (1979), pp. 307–314.
Benach et al: . . . pp. 643–649.
Todorovic et al: "Immunization Against Anaplasmosis and Babesiosis . . . ", Tropenmed Parasit., 30 (1979), pp. 43–52.

*Primary Examiner*—Blondel Hazel
*Attorney, Agent, or Firm*—Cushman, Darby & Cushman

[57] ABSTRACT

A method of preparation of babesiosis antigen including the steps of: (i) forming a crude babesiosis antigenic fraction which is derived from a lysate of Babesia infected erythrocytes or soluble fraction thereof; (ii) forming monoclonal antibody to said babesiosis antigen fraction by cloning antibody producing cells from an animal having been administered thereto said babesiosis antigen fraction; (iii) absorbing said monoclonal antibody onto an absorbent and passing said babesiosis antigenic fraction through said absorbent whereby an antigen specific to said monoclonal antibody may be bound thereto; and (iv) separating the specific antigen from the monoclonal antibody.

8 Claims, No Drawings

BABESIOSIS ANTIGEN AND METHOD FOR PREPARATION

This invention relates to a purified babesiosis antigen and method for its preparation.

Australian Patent Specification No. 63616/80 describes a method for preparation of a babesiosis vaccine which includes the steps of:
  (i) disintegration of a suspension of babesia infected erythrocytes;
  (ii) separation of the soluble and insoluble fractions contained in the disintegrated erythrocyte suspension; and
  (iii) removal of fibrinogen and contaminated babesial antigen from the soluble fraction of the disintegrated erythrocyte suspension The product of step (iii) may then be combined with an adjuvant for administration purposes.

Babesiosis is a disease that most domestic animals may experience, and it is caused by various species of the tick-born protozoan parasite Babesia. In the cattle industry in particular there are many parts of the world wherein the disease poses serious economic problems.

The vaccine prepared as described above in Australian Patent Application No. 63616/80 is useful in that it may provide protection against babesiosis as described in Patent Application No. 63616/80. However it was based on a relatively impure preparation containing many different antigens and hence it is desirable to purify this preparation to isolate the antigen or antigens which may have when used as a vaccine an effective protective or immunizing ability against babesiosis upon administration to animals and in particular cattle.

Accordingly it is the object of the present invention to provide a babesiosis antigen which when used as a vaccine is suitable for administration to animals which is a more purified antigenic preparation than that described in the prior art.

It is a further object of the invention to provide a method of preparation of the abovementioned antigen.

The method of the invention includes the steps of:
  (i) forming a crude babesiosis antigenic fraction which is preferably derived from a lysate of Babesia infected erythrocytes or soluble fraction thereof;
  (ii) forming antibody to said babesiosis antigenic fraction by cloning antibody producing cells from an animal having been administered thereto said babesiosis antigenic fraction;
  (iii) absorbing said antibody onto an absorbent and passing said babesiosis antigenic fraction through said absorbent whereby an antigen specific to said antibody may be bound thereto; and
  (iv) separating the specific antigen from the antibody.

The invention also includes within its scope a babesiosis antigen derived from passing said babesiosis antigenic fraction through an absorbent having antibody specific to said babesiosis antigen bound thereto whereby said antigen is bound to the antibody and subsequently separating said antigen therefrom.

The invention also includes within its scope a vaccine comprising said babesiosis antigen in combination with a suitable adjuvant such as oil based adjuvants including Freunds Complete Adjuvant (FCA), Freunds Incomplete Adjuvant, Adjuvant 65 and Wellcome Mineral Oil Adjuvant. Saponin aqueous solution may also be used as an adjuvant.

In step (1) a suspension of babesia infected erythrocytes may be disrupted or lysed according to the following procedures
  (i) osmotic lysis wherein the cell membrane may be disrupted in solutions of weak ionic strength;
  (ii) mechanical lysis eg sonic disintegration;
  (iii) proliferation of parasites within the cell and exiting therefrom causing breakdown of the cell membrane; and
  (iv) cell lysis wherein membranes may be lysed by specific lysins or cell antibodies.

Preferably in step (i) the cell lysate may be prepared as described by any of the methods referred to in Mahoney (1967) Exp. Parasitol 20, 232–41. Suitably, however, babesia parasite infected cells may be subjected to differential lysis in hypotonic saline. Alternatively infected cells may be lysed in 5 volumes of distilled water by osmotic pressure using a freeze and thaw technique. Alternatively the infected cells may be lysed by sonic disintegration as described in Patent Application No. 63616/80 or by the action of lytic agents such as saponin.

After lysis the cells may be centrifuged suitably at 105,000 g for 30 minutes at 5° C. and the supernatant collected.

In relation to step (i) it will also be appreciated that the soluble fraction (ie SPA) from disrupted babesia infected cells may also be prepared as described in Patent Application No. 63616/80.

In relation to step (ii) suitable animals such as mice or rats (preferably mice) may be immunized by vaccine comprising SPA in combination with a suitable adjuvant. After immunization the mice may have administered thereto antigen in the form of SPA and then killed.

Suitably antibody producing cells may then be extracted from the killed mice and fused with mouse myeloma cells.

The technique as described in Galfre et al Nature 266 550–2 (1977) may be used where polyethylene glycol may be utilized as the cell fusing agent. Preferably splenic cells from the killed mice may be fused with mouse myeloma cells to produce a hybridoma cell which then may be cloned and recloned as desired suitably on the basis of limiting dilution using mouse peritoneal cells as feeder layers. Alternatively other appropriate cloning techniques may be utilized.

When it is desired to extract antibody the cloned cells may be injected into a suitable host such as mouse wherein ascites fluid from the peritoneal cavity may be obtained having a relatively high concentration of antibody.

After production of antibody as described above from the cloned cells, the antibody may then be passed through a suitable absorption column to be absorbed onto an appropriate absorbent. In this technique the antibody may be covalently bound to the absorbent or immobile support. A suitable gel filtration technique may be utilized wherein a column comprising insoluble beads such as hydrated carbohydrate polymer (e.g. Sepharose) or other suitable immunoabsorbent. A suitable alternative may be silica beads combined with glutaraldehyde. After the antibody has been absorbed into the column, a lysate of crude babesia infected erythrocytes or alternatively SPA may be passed through the column to be covalently linked to the bound antibody.

The resulting suspension may then be passed through a chromatography column to remove unbound material as impurities. Then the column may be eluted with an appropriate agent to break the covalent bonds between the antigen and antibody with the result that the purified antigen may be collected in the eluate.

Suitable agents or elutants are salts of high ionic strength suitably having a pH greater than 7.0 or acidic solutions of low pH. An appropriate elutant is HCl dissolved in glycine buffer, citrate/citric acid, acetate/acetic acid and/or citrate/phosphate.

EXAMPLE

Immunisation of Mice

Two BALb/c mice were immunised twice, 4 weeks apart, with subcutaneous injections of equal volumes of SPA (100 μg in 0.1 ml) and Freund's Complete Adjuvant (0.1 ml) as a water-in-oil emulsion. Six weeks after the 2nd immunisation, the mice were injected intravenously with 200 μg SPA on each of three successive days and were then killed by cervical dislocation on the 4th day. Sera from the mice were monitored for antibody production using Radio Immuno Assay (RIA) and Indirect Fluorescent Antibody (IFA) tests.

Hybridoma Production

Cell fusions were performed using splenic cells from immunised mice and P3-NSI-Ag4-1 mouse myeloma cells. The method of Galfre et al. (1977) was followed using polyethylene glycol (PEG) 1500 (BDH Chemicals Ltd., England) for fusions. Cells from positive wells were cloned and recloned twice by limiting dilution using mouse peritoneal cells as feeder layers ($2 \times 10^3$ per well).

Radio Immuno Assay (RIA)

Rabbit anti-mouse globulin (Dako) was labelled with $^{125}$Iodine by the lactoperoxidase technique (Marchalonis, Biochem J. 113 299–305 (1969), and the free $^{125}$I was removed by gel filtration through a Sephadex G25 column using Phosphate Buffered Saline (PBS) as an eluting buffer. The labelled globulin was diluted in PBS to give approximately 60,000 counts per minute/5 ng globulin in 200μ/.

Antibody classes were determined using hybridoma tissue culture fluid (1/800) and class-specific rabbit antimouse antisera (Miles Laboratories, U.S.A) (1/500)+$1^{125}$Sheep antirabbit antisera ($15 \times 10^4$ CPM).

Immuno Fluorescent Staining

Thin films of B. bovis-infected erythrocytes comprising 1% infected cells and 99% uninfected cells were prepared according to the methods previously described in Goodger B. V. Int. J. Parasitol 3 387–91 (1973). Rabbit anti-mouse immunoglobulin (RVM) was prepared by previously described methods referred to in the abovementioned Goodger 1973 reference and was conjugated with fluorescein isothiocyanate (FITC) as described in the abovementioned Goodger (1973) reference. Goat anti-rabbit antisera (GvR) conjugated with FITC was obtained from Cappel Laboratories, U.S.A. Both the RvM and GvR were absorbed with an equal volume of normal bovine blood cells which had been washed three times in phosphate buffered saline i.e. PBS at a pH of 7.2 and reconstituted to a final suspension of 50%.

Neat supernatant fluid obtained from centrifugation of cloned hybridoma cells described above was applied to thin films and affixed to slides which were then incubated for 4 hr at room temperature in a humidified chamber. After 4 hr the antigen slides were washed 3 times in PBS over a 15 min period. RvM at a dilution of 1/10 in PBS was added and the slides incubated for 30 min at room temperature in a humidified chamber. The slides were then washed three times in PBS (pH 8.0) for 15 min at room temperature. Protein-A conjugated FITC (Pharmacia Fine Chemicals) was added at a dilution of 1/20 in PBS (pH 8.0) and incubated for 30 min at room temperature in a humidified chamber. The slides were again washed three times in PBS (pH 8.0) for 15 min at room temperature and mounted in 50% glycerol in PBS pH 8.0. Slides were viewed using dark ground illumination on a Leitz Ortholux microscope using a HB0200 mercury vapour lamp and a BG12 exciter filter and a K530 secondary filter.

Upon inspection of the slide under the microscope it was found in relation to clone 15B1 that the parasites in the red blood cells of the initial layer of B Bovis infected erythrocytes were intensively stained and no staining was found of the infected cell indicating that the antibody contained in the supernatant fluid was specific to the parasites. The RvM was specific to the antibody from the cloned cells (i.e. mouse anti parasite) and the GvR was specific to the RvM. The protein A was specific to the GvR and the use of FTIC in protein A, GvR and RvM enhanced the fluorescent reaction between the parasites in the erythrocytes and the film of mouse anti parasite antibody.

The experiment was repeated in its entirety using ascites fluid from mice previously injected with cloned hybridoma cells described above. Instead of the supernatant fluid ascites fluid was derived from the abdomen of mice and contained high levels of antibody. Similar results were obtained.

In relation to storage of hybridoma cell lines, these were stored in the vapour phase of liquid nitrogen ($1 \times 10^7$ cells in 1 ml of 90% foetal calf serum and 10% dimethyl sulphoxide).

The ascites fluid referred to above was produced by priming BALb/c mice with 100 mg Pristane (Aldrich Chemicals USA) by intra peritoneal (IP) injection 7-10 days prior to IP injection of $1 \times 10^8$ cloned cells. Ascites fluid was collected 10-14 days later. Non globulin proteins were removed by precipitation with RIVANOL (Monstratos and Beswick J. Path 98, 17–24 (1969). The supernatants containing immunoglobulins were stored as small aliquots at −20° until required.

Immuno Absorption

Five g CNBr Sepharose 4B (Pharmacia) was cross reacted with mouse ascites fluid containing 100 mg globulin. The globulin of mouse ascites fluid was precipitated at room temperature with 30% saturated ammonium sulphate dissolved in a minimal volume of carbonate-bicarbonate buffer pH8 and dialysed against the latter for 24 h at 4°. An aliquot containing 100 mg protein was then coupled to 5 g CNBr Sepharose 4B (Pharmacia) according to the manufacturer's instruction. Ten ml crude of B. bovis lysate was then added to the activated immuno absorbant (IA) and the suspension mixed by gentle shaking for 2 hr at room temperature. The suspension was then poured into a $20 \times 1$ cm chromatography column and unbound material removed by washing with PBS until no further material could be detected at 280 nm. The column was then washed free of non-covalently bound proteins with borate buffer 0.1M pH9.0 containing 0.1% Tween 20. When the absorbance was again zero, the column was eluted with 0.1M glycine/HCl buffer pH3.3 containing 1M NaCl. Eluate fraction having absorbances of >0.01 at 280 nm were pooled, neutralized, and dialysed against PBS. The column was regenerated by washing with PBS. If required the absorbance of eluate fractions was obtained at 413 nm.

Electrophoresis

Eluate from immunoadsorption columns was analysed by gradient acrylamide electrophoresis (Margolis and Kerrick, Anal Biochem 25 347–62 (1968) using normal bovine plasma as a reference. It was also analysed by solium dodecyl sulphate (SDS) electrophoresis (Weber and Osborne, (1969) J. Biol Chem 244 4406–12) after treatment the SDS or SDS-mercaptoethanol (ME). The latter was used for molecular weight estimations from comparison with known standards (Boehringer). In both procedures proteins were stained with 0.1% Amido Black 10B and destained in 5% acetic acid.

Western Blotting

Following electrophoresis, the proteins in gel slabs were electrophoretically transferred to cellulose nitrate sheets (Biorad Labs) according to the method of Towbin et al. (1979) Proc Natl Acad. Sci USA 76 4350–54 with the exception that methanol was deleted from transfer buffers. Proteins which were babesial antigens were detected in the sheets by sequential application of bovine anti-B. bovis serum, goat anti-bovine IgG conjugated to peroxidase (CSL) and napthal-hydrogen peroxide using buffers dilutions and incubation times as suggested by Hawkes et al. (1982) Anal Biochem 119 142–147.

Bovine Antisera

Bovine antisera to the B. bovis Samford and Lismore strains and to the Glenlogan strain were used to determine cross reactivity of antigens purified by imunoabsorption techniques. Both the Samford and Lismore strains of B. bovis have been held as stabilates both by tick-transmission and in the vapour phase of liquid nitrogen in our laboratories for many years.

RESULTS

Eluate of B. bovis lysate from 1A columns contained 500 μg protein and produced 2 bands with SDS—Mercaptoethanol electrophoresis, one with a molecular weight of $29 \times 10^3$, and the other with the characteristics of a haem component. This eluate, when used as the antigen in RIA reacted strongly with bovine antisera derived from three distinct strains. This cross-reactivity could be inhibited with prior incubation of 15B1 antibodies and the eluate. The band with a molecular weight of $29 \times 10^3$ was a single peptide chain in both denaturing and under reducing-denaturing conditions.

The results of the Western Blotting test indicated a single band corresponding to a protein of molecular weight $29 \times 10^3$ and thus gave a similar result as described above for the electrophoresis test. Antisera derived from animals immunised with either B. bovis (Samford Strain) or B. bovis (Lismore Strain) or B. bovis (Glenlogan Strain) demonstrated that the eluate from B. bovis lysate from 1A column was a single protein of MW 44,000 under native conditions.

Immunisation Regime

Four susceptible splenectomised calves were vaccinated twice, 4 weeks apart with 100 μg of eluate from the 1A column as a water-in-oil emulsion with equal volumes (1.5 ml of each) of Freunds Complete Adjuvant. Seven weeks after the first injection these animals and a similar group of susceptible splenectomised control calves were challenged with $1 \times 10^4$ homologous virulent B. bovis organisms. All control calves died 9 days post injection, but only one vaccinated animal died, 12 days post injection. The vaccinated group had significantly lower temperature rises ($p<0.05$) haematocut fall ($p<0.05$) and parasitaemia (mean highest value controls $400 \times 10^3/\mu l$ blood on day 9, vaccinated $42 \times 10^3$ ml blood on day 9 ($p<0.001$).

These data are comparable to that obtained under similar conditions by Goodger, et. al. 1981 Parasitenkunde 66 41–48 using a crude extract from disintegrated B. bovis-infected enythrocytes.

I claim:

1. A method for preparation of babesiosis antigen including the steps of:
   (i) forming a crude babesiosis antigenic fraction which is derived from a lysate of Babesia infected erythrocytes or soluble fraction thereof;
   (ii) forming monoclonal antibody to said babesiosis antigenic fraction by cloning antibody producing cells from an animal having been administered thereto said babesiosis antigenic fraction;
   (iii) absorbing said monoclonal antibody onto an absorbent and passing said babesiosis antigenic fraction through said absorbent whereby an antigen specific to said monoclonal antibody may be bound thereto; and
   (iv) separating said specific antigen from the monoclonal antibody.

2. A method as claimed in claim 1, wherein said soluble fraction is formed by centrifugation of said infected erythrocytes and collection of the supernatant.

3. A method as claimed in claim 1, wherein in step (ii) said animal is immunized with a vaccine comprising said soluble fraction in combination with an adjuvant and subsequently said animal is administered antigen in the form of said soluble fraction and then killed whereafter said antibody producing cells are extracted.

4. A method as claimed in claim 3, wherein said antibody producing cells are fused to mouse myeloma cells to produce a hybridoma cell which is cloned and recloned on the basis of limiting dilution using mouse peritoneal cells as feeder layers.

5. A method as claimed in claim 4, wherein said cloned cells are injected into a mouse wherein ascites fluid from a peritoneal cavity of said mouse is obtained having a relatively high concentration of monoclonal antibody.

6. A method as claimed in claim 4, wherein wherein in step (iii) a lysate of crude babesia infected erythrocytes or said soluble fraction is passed through a gel filtration column having said monoclonal antibody absorbed thereon, to be covalently bound to said monoclonal antibody thus forming a suspension.

7. A method as claimed in claim 6, wherein said suspension is passed through a chromatography column to remove impurities and then said chromatography column is eluted to collect purified antigen in the eluate.

8. A method as claimed in claim 7, wherein said column is eluted with an acidic solution of relatively low pH in combination with a salt of a high ionic strength having a pH greater than 7.0.

* * * * *